US009305551B1

(12) United States Patent
Johns et al.

(10) Patent No.: US 9,305,551 B1
(45) Date of Patent: Apr. 5, 2016

(54) SCRIBE SYSTEM FOR TRANSMITTING AN AUDIO RECORDING FROM A RECORDING DEVICE TO A SERVER

(71) Applicants: Timothy A. Johns, Mesa, AZ (US); Bryan McCormick, Mesa, AZ (US)

(72) Inventors: Timothy A. Johns, Mesa, AZ (US); Bryan McCormick, Mesa, AZ (US)

( * ) Notice: Subject to any disclaimer, the term of this patent is extended or adjusted under 35 U.S.C. 154(b) by 121 days.

(21) Appl. No.: 13/960,401

(22) Filed: Aug. 6, 2013

(51) Int. Cl.
*G10L 15/00* (2013.01)
*G10L 15/04* (2013.01)
*G10L 21/00* (2013.01)
*G10L 25/00* (2013.01)
*G10L 15/26* (2006.01)

(52) U.S. Cl.
CPC .................................. *G10L 15/26* (2013.01)

(58) Field of Classification Search
USPC .................. 704/231–257, 270–275
See application file for complete search history.

(56) References Cited

U.S. PATENT DOCUMENTS

| 5,126,543 | A | 6/1992 | Bergeron et al. |
| 5,163,085 | A | 11/1992 | Sweet et al. |
| 5,898,916 | A | 4/1999 | Breslawsky |
| 6,173,259 | B1 * | 1/2001 | Bijl et al. ..................... 704/235 |
| 6,175,822 | B1 | 1/2001 | Jones |
| 6,215,992 | B1 | 4/2001 | Howell et al. |
| 6,259,657 | B1 * | 7/2001 | Swinney ..................... 704/270 |
| 6,658,384 | B2 | 12/2003 | Swinney |
| 7,039,586 | B2 | 5/2006 | Swinney |
| 7,054,863 | B2 | 5/2006 | Lasensky et al. |
| 7,203,288 | B1 | 4/2007 | Dwyer et al. |
| 7,558,735 | B1 | 7/2009 | Obilisetty |
| 2002/0178002 | A1 * | 11/2002 | Boguraev et al. ............. 704/235 |
| 2004/0202291 | A1 | 10/2004 | Skinner |
| 2004/0204938 | A1 * | 10/2004 | Wolfe et al. .................... 704/235 |
| 2005/0096906 | A1 * | 5/2005 | Barzilay ...................... 704/249 |
| 2005/0124383 | A1 | 6/2005 | Booth |
| 2005/0154586 | A1 * | 7/2005 | Liu .............................. 704/235 |
| 2006/0256933 | A1 | 11/2006 | Wolfe et al. |
| 2007/0127640 | A1 * | 6/2007 | Brunel ....................... 379/88.13 |
| 2008/0119239 | A1 * | 5/2008 | Mabuchi .................... 455/569.1 |
| 2008/0154598 | A1 | 6/2008 | Smith |
| 2008/0169903 | A1 * | 7/2008 | Fein et al. .................... 340/5.84 |
| 2009/0070109 | A1 * | 3/2009 | Didcock et al. .............. 704/235 |
| 2009/0177470 | A1 * | 7/2009 | Beach et al. .................. 704/235 |

* cited by examiner

*Primary Examiner* — Jesse Pullias
(74) *Attorney, Agent, or Firm* — Schmeiser, Olsen & Watts LLP

(57) ABSTRACT

A scribe system is provided. The scribe system includes a server operating a software product and a plurality of recording devices for recording speech of a user into a recorded audio file. The scribe system also includes a network connection between the server and the plurality of recording devices. Each recording device transfers the recorded audio file to the server through the network connection in response to completion of recording the audio file. The server confirms successful transmission to the recording device in response to operation of the software product.

13 Claims, 4 Drawing Sheets

SCRIBE SYSTEM FOR TRANSMITTING AN AUDIO RECORDING FROM A RECORDING DEVICE TO A SERVER

BACKGROUND OF THE INVENTION

1. Technical Field

This invention relates generally to a transcription system and more particularly to a remote scribe system utilizing wireless technologies to transfer voice files.

2. State of the Art

There are several industries and professions that require or are benefited from the use of a transcription service. For example, doctors often make dictates notes and records them on a hand held voice recorder, wherein the doctor then uploads the sound file and sends it to his or her transcriptionist in order to place his notes into a written note for the patient file and medical records. This becomes a tedious and time consuming task for professionals who must use transcription on a daily basis.

Some conventional ways of making this task easy have been explored. One conventional system and method for originating, storing, processing and delivering message data includes a communication system that has a transmitting device that communicates with a server over a network. The data is stored and is accessible by one having privilege to do so, by accessing the network from a computer or similar type of device, like a PDA, a phone, etc.

Another conventional system includes a transcription application infrastructure and methodology that uses a remote device to send a voice file containing a digital recording of the dictated information over the Internet to a transcription service provider. The voice file, as transcribed information, is sent to the end user by use of fax or even through the Web. In particular embodiments, the sending of the voice file may be initiated with a telephone connection, wherein the dictation is captured over the telephone, digitized and sent via the Internet to the service provider.

Other conventional systems include intelligent routing of voice files in voice data management system. These systems use a portable digital voice recorder that interfaces with a computer to transfer stored voice data files from the recorder to the computer. This transfer of voice data files may be performed wirelessly.

Some conventional systems use a wireless communication device that communicates with a computer and/or a server to transmit a way file of the dictation to the computer and/or server. Other systems operate by capturing digital audio files at a messaging server, and storing the audio files in a message store. The system is configured to stream a digital audio file over a data network to a transcription terminal, wherein a transcriptionist transcribes the audio file.

Each of these systems has limitations. For example, but not limited to, these conventional systems do not allow for a recording device that is remote and caches the voice data local on the device while transmitting the voice file to a remote server. Further, the recording devices of these conventional systems do not provide for two way communication, such as feedback communication. Further, these systems do not provide for on-board encryption of the voice file on the recording device. At least these limitations are known with the recording device and other limitations regarding the scribe systems discussed above exist, for which there is need for improvement.

Accordingly, there is a need in the field of scribe systems, for an improved scribe system with improved capabilities of the recording device along with improved capabilities of the transcriptions portion of the scribe system.

DISCLOSURE OF THE INVENTION

The present invention relates to a scribe system that includes remote recording device, wherein the remote recording device is in communication with a server that operates software to control the transcription purposes of the system.

Embodiments include a scribe system comprising a server operating a software product; a plurality of recording devices for recording speech of a user into a recorded audio file; and a network connection between the server and the plurality of recording devices, wherein each recording device transfers the recorded audio file to the server through the network connection in response to completion of recording the audio file; and the server confirms successful transmission to the recording device in response to operation of the software product.

Embodiments also include a method of using a scribe system to record information and store on a server, the method comprising starting a recording function of a recording device; recording a user speaking into a microphone of the recording device; processing the recorded audio file; and transmitting the recorded audio file to a server for storage.

Further, embodiments include a method of using a scribe system after a recorded audio file is transmitted to the server, the method comprising queuing all transmitted recorded audio files in a database; allocating the workload of all transcribers of the system in response to operation of the software product; assign a recorded audio file to a transcriber with the least workload; transcribing the recorded audio file; and entering the transcribed information into an electronic medical record of a patient.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

As discussed above, embodiments of the present invention relate to a scribe system that includes remote recording device, wherein the remote recording device is in communication with a server that operates software to control the transcription purposes of the system.

Figure 1:
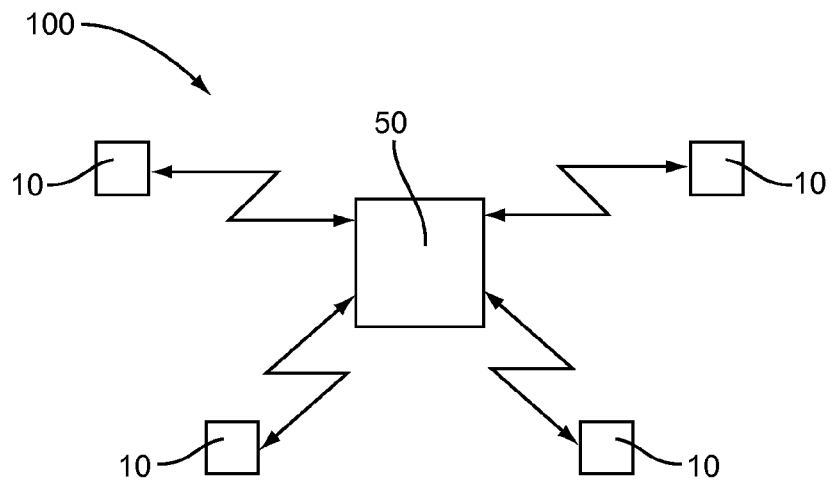
FIG. 1 is a schematic view of a scribe system.

Referring to the drawings, FIG. 1 depicts a scribe system 100 comprises a digital scribe server 50 in communication with a recording device 10. The recording device 10 may be a remote recording device 10 that is in wireless communication with the server 50.

Figure 2:
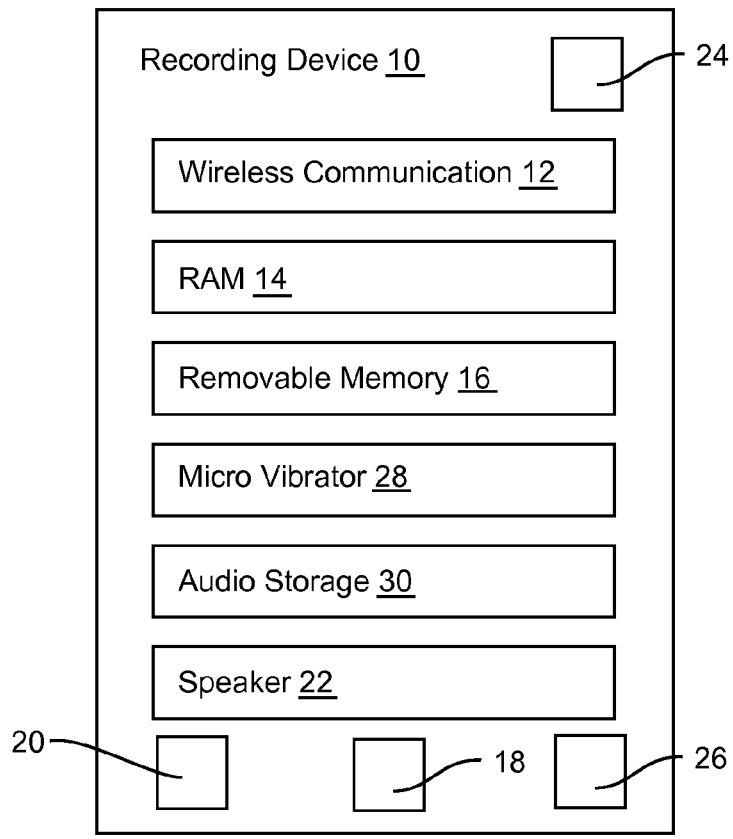
FIG. 2 is a schematic view of a recording device of a scribe system.

Referring to the drawings, FIG. 2 depicts a recording device 10 of a scribe system according to a particular embodiment of the present invention. The recording device 10 comprises a wireless communication device 12, RAM 14, removable memory 16, connection port 18, a microphone 20, a speaker 22, an LED 24, a button 26, a micro vibrator 28 and audio storage 30.

The wireless communication device 12 provides a secured communication link with the server 50 through various wireless technology platforms, such as, but not limited to, Wi-Fi, Bluetooth, IR, RF and the like, including other wireless technology that may be obtainable in the future, so long as the wireless communication allows for encrypted transmission of voice files.

The RAM 14 allows for certain functionality of the recording device 10, such as, but not limited to an encryption of the files. The removable memory 16 operates to store voice files that are recorded by a user using the recording device 10. The removable memory may be overwritten. The removable memory 16 operates as a cache of the information and voice files recorded on the recording device 10. The voice files are encrypted and stored, wherein access to the voice files is inhibited by the encryption. This is particularly important given the personal nature of the information being recorded. Particularly in a health related field, wherein the information includes medical history of a patient, the voice filed must be encrypted locally on the recording device 10, in transmission and on the server 50 in order to comply with HIPPA policies.

The connection port 18 operates to allow transfer of information and also functions as a port to charge the recording device. For example, without limitation, the connection port 18 may be a USB port that allows for the transfer of information and data between the recording device 10 and the server 50. The USB port 18 also allows for charging of the recording device 10. This is true whether the connection port 18 is connected to a computer or to an external power source, such as a wall outlet.

The microphone 20 is used to capture and record the voice of the user as the user dictates to the recording device. The microphone 20 in particular embodiments may be a high-definition microphone, wherein the high-definition microphone 20 allows for the cancellation of back ground noise in order to the clearly discern the user's voice and dictation. The microphone 20 operates in the same fashion as conventional microphones.

The speaker 22 of the recording device 10 may be present in some embodiments. The speaker 22 allows the user to hear certain audio on the recording device 10. One example of audio played through the speaker 22 is audible tones wherein the audible tones are determined from the audio storage 30. The audio storage contains pointer to particular tones that indicate a certain status of the recording device or other status of the system 100. As the recording device 10 receives messages regarding the status of any component of the system 100, including the status of any component of the recording device 10, the audio storage 30 allows for the playing of the audible sound that indicates that particular status event.

The speaker 22 may also be used to receive audio messages from the server and further may be used to replay the dictation previously made by the user, wherein the user may then accept the dictation and finalize it. The use of the speaker 22 is controlled by the system, wherein hardware or software considerations determine what types of audio is playable by the recording device 10 and thereby heard through the speaker 22.

The LED 24 is contemplated to operate as a communication device to the user, wherein the flash pattern and/or color of the LED 24 corresponds to a particular status of the recording device 10. For example, and without limitation, Table 1 indicates exemplary LED indications.

TABLE 1

LED Flash Patterns/Colors and Status Indications

| Flash Pattern and Color | Status Indication |
| --- | --- |
| Constant Blink Red - 1 second interval | Default factory configuration |
| Constant Blink Green - 1 second interval | Configured to be tested |
| Green Blink - 10 second interval | Device is configured and ready for use |
| Steady Amber | Recording audio |
| Steady Red | Device fault - check diagnostic logs |
| Amber 3 Blink | Low battery (10% or below) |
| Amber 4 Blink | Battery critical |
| Alternating Green/Amber - 30 second interval | Messages waiting to be transmitted |

Figure 5:
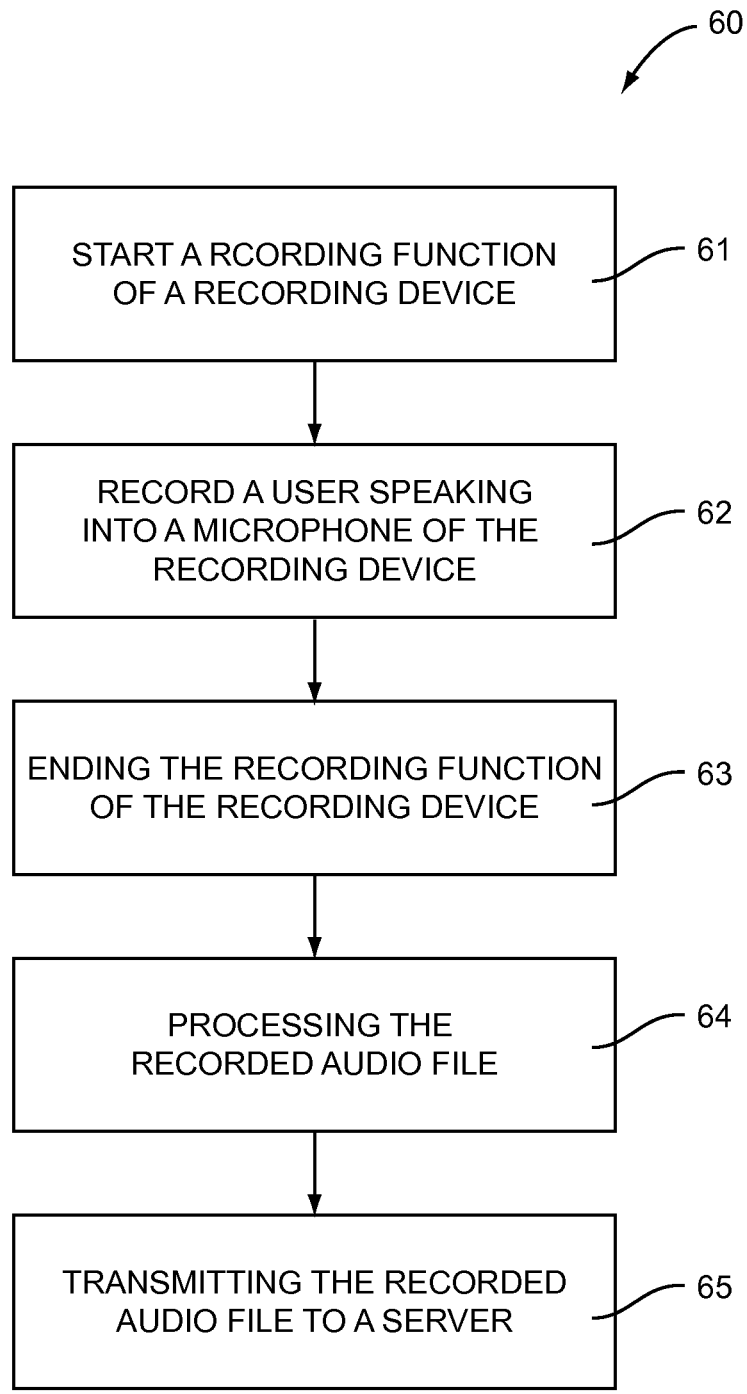
FIG. 5 is a flow chart of a method of using a scribe system to record and transmit a voice file to the server.

A button 26 of the recording device 10 functions to provide the user and activation source for use of the recording device 10. Referring further to FIG. 5, a method 60 of using a scribe system includes pressing the button 26 one time to initiate a record function (Step 61); speaking into the microphone 20 to record (Step 62); pressing the button 26 to complete the recording (Step 63); and pressing the button in a particular pattern to optionally perform tasks with the recorded voice file (Step 64). For example, Table 2 shows operations corresponding to button 26 presses after the recording is completed.

TABLE 2

Button Pressing Pattern and Corresponding Operation

| Button Pressing Pattern | Operation |
| --- | --- |
| Press one time | Replay |
| Press two times | Accept file, write to removable memory 16 and transmit to server 50 |
| Press three times | Re-record |
| No action | Accept file, write to removable memory 16 and transmit to server 50 |

The micro vibrator 28 of the recording device operates as a feedback communication device. The micro vibrator 28 may vibrate in order to provide messages, or feedback messages to the user. For example, if the recording device 10 changes status and the LED 24 is blinking, the micro vibrator 28 may also vibrator to notify the user to look at the recording device 10 and determine the status. Additionally, if the server 50 functions to send a message to the recording device 10, the micro vibrator 28 may vibrate to notify the user of the pending message. The micro vibrator may also vibrate for other communication needs as determined by the system 100 and the software 56 operating on the server 50.

As shown in FIG. 1, a plurality of recording device 10 may be used in the scribe system 100. Each recording device 10 may be used, for example, by a different doctor working in a hospital. The recording devices 10 may include a unique identifier. This identifier may include a name, a number, symbols, combinations thereof, and further may include an IP address or mac address. The identifier is critical in operation of a scribe system 100 with multiple recording devices. Because the recording devices 10 manually and automatically transmit the voice files to the server, it is critical that the server can discern what user recorded the voice file so as to properly sort and determine what user is associated with what patient and further to determine what scribe receives the files for transcription.

It is contemplated that in some embodiments specific device will have a single identifier that is associated with particular recording device 10 and a particular user. In this configuration, only the user associated with the identifier of the particular recording device 10 is allowed to operate the recording device 10. In these embodiments, the recording device 10 may also have a roaming wireless profile, wherein as the user moves from site to site, wherein each site uses the scribe system 100.

In other embodiments, each recording device 10 has a specific non-changing identifier, and a user checks out the recording device 10, wherein the system records what device that particular user checked out that day and associates the recorded voice files transmitted to the server that day from that recording device 10 to the user that checked it out.

Figure 3:
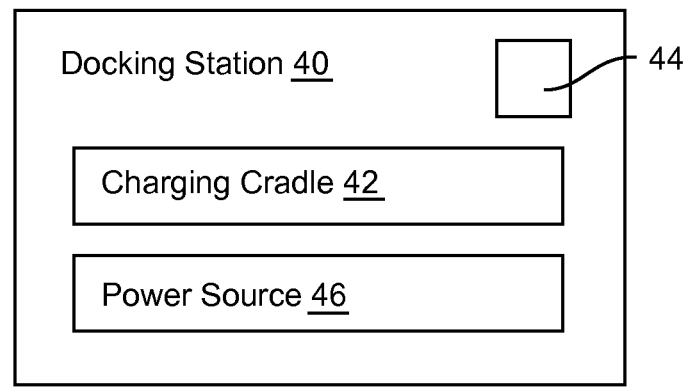
FIG. 3 is a schematic view of a docking station for the recording devices of a scribe system.

Referring again to the drawings, FIG. 3 depicts a docking station 40 of a scribe system according to a particular embodiment of the present invention. The docking station comprises a charging cradle 42, a charging indicator 44 and a power source 46. The charging cradle 42 is configured to receive a recording device 10, wherein the recording device 10 plugs into a connection that allows transfer of power from the power source 46 to the recording device 10. The charging indicator 44 lights a particular color to indicate that the recording device 10 is charging. The color of the charging indicator 44 changes with the recording device 10 is fully charged. The docking station 40, in some embodiments may have a plurality of charging cradles 42, wherein each charging cradle 42 has a corresponding charging indicator 44. The docking station 40 also serves as a point to allow direct communication with a digital scribe server. Accordingly, the docking station 40 may be in communication with the digital scribe server through a network connection. This network connection allows transfer of data between the recording device 10 and the digital scribe server.

Figure 4:
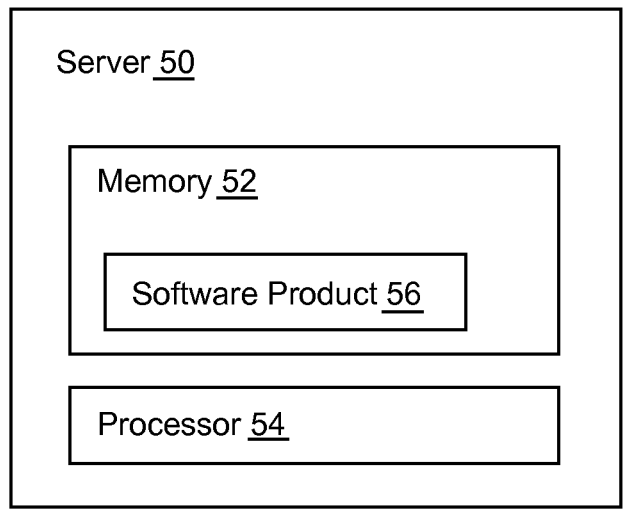
FIG. 4 is a schematic view of a server of a scribe system.

Referring to FIG. 4, embodiments of the scribe system include a digital scribe server 50. The server 50 comprises a memory 52, and a processor 54, wherein the server is a computer that operates a software product 56 stored on the memory 52 by use of the processor 54. The software product 56 functions to operate the entire scribe system on the digital server 50 end. The server 50 is in communication with the recording device 10.

The software product 56 operates as a middleware and provides several functions related to communication and management of data in the scribe system. One embodiment of the software product 56 provides communication between the server 50 and the recording device 10. The software product 56 receives data from the recording device 10 and then transmits it to the server 50, and also receives data from the server 50 and transmits it to the recording device 10.

Referring to the software product 56 functions, the following is to be understood as an example of an embodiment, wherein other features and operations may be available. The server 50 may provide firmware and firmware updates to the software product 56, wherein the software product 56 sends the firmware or firmware update to the recording device 10. The software product 56 ensures that the file containing the firmware information has the proper header and other information for the recording device 10 to recognize the data as firmware or a firmware update. The recording device 10 may then install the firmware or firmware update.

Further, the software product 56 may receive data from the recording device 10 in the form of a recorded audio file. The recording device transmits the recorded audio file through a network connection to the server 50, wherein the software product 56 accesses the audio file and processes it in order to determine if the audio file is proper, has transferred correctly and if the transfer is correctly made, saves the file to the server 50. If the transmission of the audio file is not completed properly, the software product 56 sends a notification to the recording device 10. The notification sent to the recording device 10 provides operational instructions for the recording device 10 to maintain the audio file on local storage and queue the audio file for another transfer.

Additionally, the software product 56 may also be used to send feedback to the recording device 10. Typically, this is follow-on information, such as, but not limited to a pre-recorded message that is user defined. These messages may tell information related to the system, related to data being transferred, and messages related to the status of the device. For example and without limitation, the software product 56 may send messages such as "connected to wireless network," "not connected to wireless network," "file transmitted successfully," and "error transmitting file." In some embodiments, the software product 56 does not send the actual messages, but rather the recording device 10 has predefined messages stored in local memory and the software product 56 sends a trigger to tell the recording device 10 what message to relay through the recording device 10.

In some embodiments, these messages will be delivered to the user of the recording device by an audible played message; in other embodiments, these messages may be delivered to a screen display for the user to read; and further still in other embodiments, the messages may be delivered to LEDs, wherein the LEDs have certain colors or blinking patterns to provide the user with the intended information. Additionally, a combination of these forms of messages may be utilized.

Further, in embodiments, the user may perform steps in order to obtain messages from the server. For example, the user may activate a message receiving function of the recording device 10. This may be done by pressing a button or pressing the record button a set amount of times in order to activate the message receiving function. Once this function is activate, the recording device automatically pings the server to see if there messages waiting. The software product 56 sends a confirmation of whether a message is waiting, if there is not a message, the device automatically ends the message receiving function. If there are messages waiting, the recording device downloads the messages and the software product 56 marks the message as received on the server 50. Once the message is received, the recording device automatically plays the message. The user may then replay, save or delete the message.

With reference to FIG. 5, a method 60 of using a digital scribe system to record and transmit audio to a server is depicted. The method 60 includes a step of starting a recording function of a recording device (Step 61). In embodiments, Step 61 of starting a recording function may include pressing a button on the recording device to activate the recording function. Once the recording device initiated the recording function, the device records a user speaking into a microphone of the recording device (Step 62). In some embodiments, the recording device encrypts the audio file as it is being recorded for additional safety. Further, recording of the audio file while the user speaks comprises recording it to RAM. When the user has completed speaking, the method 60 includes ending the recording function of the recording device (Step 63). Step 63 of ending the recording function may include pressing a button to end the recording.

After the recording function is ended, the method 60 also includes processing the recorded audio file (Step 64). Step 64 of processing the recorded audio file may include several processes. Step 64 may include performing a playback of the recorded audio file. This allows for the user to determine if he or she has recorded the desired information clearly. Step 64 may also include accepting the recording and writing it to the local memory of the recording device, wherein writing it to the local memory may include encrypting the file, adding a header and adding a tail, wherein the header and tail provide information for the software product 56 to properly process the audio file during transmission to the server to ensure that the audio file was properly transmitted. It will be understood that the writing of the audio file to the local memory of the recording device may be user actuated or automatically performed after a predetermined lapse of time. Step 64 may also include re-recording the audio file.

Once Step 64 of processing the recording audio file is complete, the method 60 comprises transmitting the recorded audio file to a server (Step 65). Step 65 of transmitting the recorded audio file may be user initiated or automatically sent at a predetermined time of day, time lapse after recording, or upon connecting the recording device to a docking station. Step 65 may also include authenticating the recording by the software product and confirming a complete transfer of the file. The method 60 may also include steps of notifying the recording device of successful or unsuccessful transmission of the recorded audio file. If the transmission notification of the recording device indicates successful transmission, the recording device automatically deletes the recorded audio file. It will be understood that the method 60 conforms to HIPAA standards.

Figure 6:
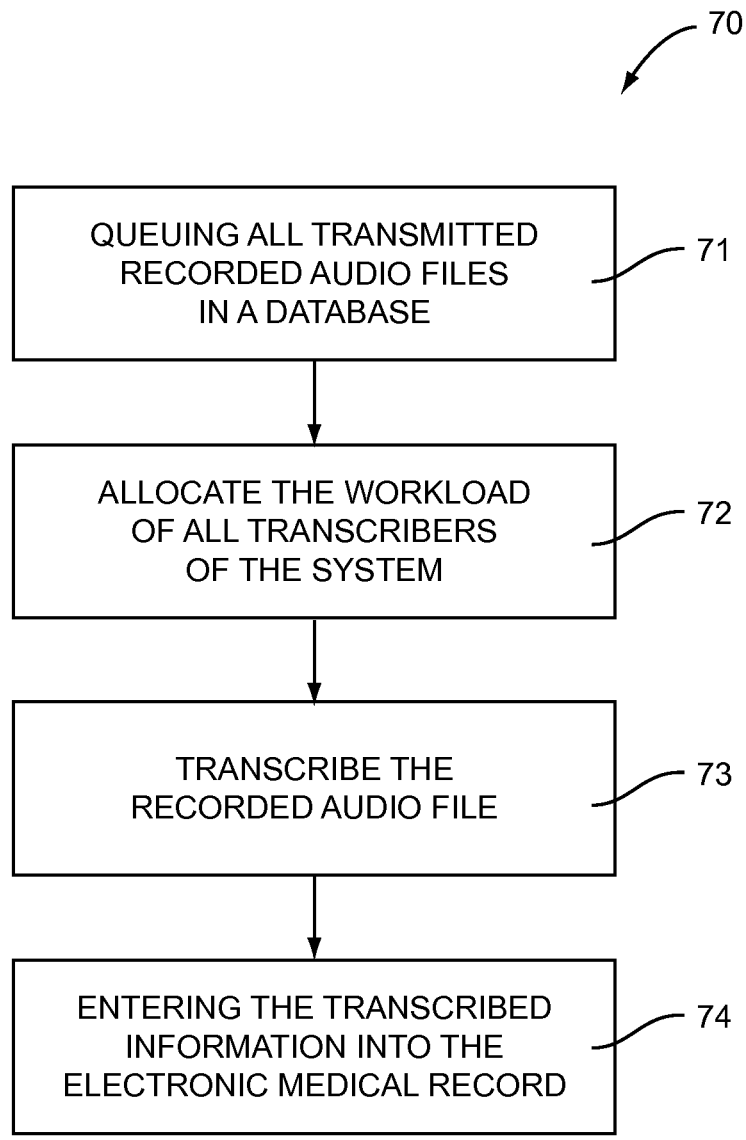
FIG. 6 is a flow chart of method of using a scribe system after receiving a communication from the server.

Once the transmission is completed, method 70 of using the scribe system after the recording is transmitted to the server is then utilized, as depicted in FIG. 6. The method 70 comprises queuing all transmitted recorded audio files in a database (Step 71). This database may be stored on memory of the server. Once the recorded audio files are stored in the database during Step 71, the system allocates the workload of all transcribers of the system in response to operation of the software product (Step 72). Step 72 may include determining how many recorded audio files have been assigned to each transcriber and then send a recorded audio file to the transcriber with the least amount of files in his or her personal transcription queue.

Once an audio file is assigned to a transcriber in step 72, the transcriber then transcribes the recorded audio file (Step 73). Transcribing in Step 73 may be manual transcribing accomplished by a person who listens to and types the words played from the recorded audio file. Other embodiments include automated transcribing by use of computing device with capabilities to translate speech-to-text, wherein a person would then verify the accuracy of the transcription performed by the computing device. Once the transcribing is completed in Step 73, the method 70 includes entering the transcribed information into the electronic medical record of a patient to which the transcribed information refers to (Step 74). This may be performed manually or automatically.

The method 70 may include additional steps, such as decrypting the audio file, and saving the recorded audio file after transcription is completed. It will be understood that the method 70 may be performed over a web based application, wherein transcribers access the recordings through a web portal or the like and perform the transcription services through the portal.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A scribe system comprising:
a server operating a software product;
a plurality of recording devices for recording speech of a user into a recorded audio file; and
a network connection between the server and the plurality of recording devices, wherein:
  each recording device transfers the recorded audio file to the server through the network connection in response to completion of recording the audio file; and
  the server sends a notification the recording device to confirm successful transmission to the recording device in response to operation of the software product, wherein the recording device automatically deletes the recorded audio file, or the server sends a notification of unsuccessful transmission to the recording device in response to operation of the software, wherein the unsuccessful transmission includes operational instructions for the recording device to maintain the audio file on local storage and queue the audio file for another transfer.

2. The system of claim 1, wherein each recording device comprises a wireless communication device; RAM; removable memory; a microphone; a button; a micro vibrator; and audio storage.

3. The system of claim 2, wherein each recording device records speech of the user in response to pressing the button.

4. The system of claim 3, wherein speech of the user is saved in an audio file in the RAM and written to the removable memory in response to one of manual pressing of the button or automatically at lapsing of a predetermined time.

5. The system of claim 1, wherein the software product sends notifications to the recording device from the server.

6. The system of claim 5, wherein the notifications are one of transmission successful or transmission unsuccessful.

7. The system of claim 6, wherein the recording devices deletes the recorded audio file in response to receiving the transmission successful notification from the software product.

8. A method of using a scribe system to record information and store the information on a server, the method comprising:
starting a recording function of a recording device;
recording a user speaking into a microphone of the recording device;
processing the recorded audio file;
transmitting the recorded audio file to a server for storage;
authenticating the recorded audio file by a software product operated on the server and confirming a complete transfer of the file; and
sending a successful transmission notification or an unsuccessful transmission notification to the recording device from the server in response to confirming the complete transfer of the file, wherein:
  the recording device automatically deletes the recorded audio file in response to receiving a successful transmission notification, or the server sends a notification of unsuccessful transmission to the recording device in response to operation of the software, and
  the unsuccessful transmission includes operational instructions for the recording device to maintain the audio file on local storage and queue the audio file for another transfer.

9. The method of claim 8, wherein starting the recording function comprises manually pressing a button on the recording device.

10. The method of claim 8, wherein recording a user speaking further comprises encrypting the audio file as it is being recorded.

11. The method of claim 8, wherein recording the user speaking comprises recording the audio file to RAM.

12. The method of claim 8, wherein ending the recording function comprises pressing a button of the recording device.

13. The method of claim 8, wherein processing the recorded audio file comprises one of performing a playback of the recorded audio file, writing the recorded audio to a removable memory of the recording device or re-recording the audio file.

* * * * *